(12) United States Patent
Kirkwood et al.

(10) Patent No.: US 12,109,152 B2
(45) Date of Patent: Oct. 8, 2024

(54) MODIFICATION TO LEADED EYEWEAR FOR SIGNIFICANT OPERATOR EYE RADIATION DOSE REDUCTION

(71) Applicant: THE BOARD OF REGENTS OF THE UNIVERSITY OF TEXAS SYSTEM, Austin, TX (US)

(72) Inventors: Melissa Kirkwood, Dallas, TX (US); Jeffrey Guild, Arlington, TX (US); Gary Arbique, Austin, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 17/763,983

(22) PCT Filed: Sep. 25, 2020

(86) PCT No.: PCT/US2020/052803
§ 371 (c)(1),
(2) Date: Mar. 25, 2022

(87) PCT Pub. No.: WO2021/062211
PCT Pub. Date: Apr. 1, 2021

(65) Prior Publication Data
US 2022/0370248 A1 Nov. 24, 2022

Related U.S. Application Data

(60) Provisional application No. 62/907,005, filed on Sep. 27, 2019, provisional application No. 63/037,813, filed on Jun. 11, 2020.

(51) Int. Cl.
*A61F 9/02* (2006.01)

(52) U.S. Cl.
CPC .............. *A61F 9/025* (2013.01); *A61F 9/029* (2013.01)

(58) Field of Classification Search
CPC .......... A61F 9/025; A61F 9/029; A61F 9/045; A61F 2013/00497; A61F 2013/00502; G02C 7/16; G02C 11/12
See application file for complete search history.

(56) References Cited

U.S. PATENT DOCUMENTS 1,706,682 A * 3/1929 Takacs ................... G02C 11/12
                                                        2/13
4,021,862 A    5/1977 Glasser
(Continued)

FOREIGN PATENT DOCUMENTS

EP        3348244 A1    7/2018

OTHER PUBLICATIONS

Cigna Healthcare Facial bones, dated Jul. 18, 2023, retrieved by Examiner at https://www.cigna.com/knowledge-center/hw/facial-bones-aa60007 on Dec. 29, 2023 (Year: 2023).*
(Continued)

*Primary Examiner* — F Griffin Hall
(74) *Attorney, Agent, or Firm* — DLA Piper LLP US

(57) ABSTRACT

The present disclosure provides a removable eyewear shielding device, an eyewear comprising a removable eyewear shielding device, and methods of uses thereof for reducing eye radiation exposure, reducing ipsilateral brain radiation exposure, reducing FGI-induced lens opacification, reducing cataract development, or protecting an eye or ipsilateral brain from radiation exposure.

23 Claims, 9 Drawing Sheets

(56) References Cited

U.S. PATENT DOCUMENTS

| | | | |
|---|---|---|---|
| 4,729,650 A | | 3/1988 | Jennings |
| 4,751,746 A | * | 6/1988 | Rustin .................. A61F 9/029 D16/330 |
| 4,856,535 A | | 8/1989 | Forbes |
| 4,944,039 A | | 7/1990 | Dietrich |
| 5,704,063 A | * | 1/1998 | Tilden ................ A41D 13/1161 2/427 |
| 6,393,609 B1 | | 5/2002 | Simmons |
| 6,540,347 B1 | * | 4/2003 | Radziwon .............. G02C 11/00 2/13 |
| 6,832,389 B2 | * | 12/2004 | Simmons, Sr. .......... G02C 7/16 351/158 |
| 8,387,163 B2 | * | 3/2013 | Beliveau ................ A41D 13/11 128/857 |
| 9,046,701 B2 | * | 6/2015 | Nodtvedt ................ G02C 11/00 |
| 9,675,121 B1 | | 6/2017 | Everest |
| 9,989,783 B1 | * | 6/2018 | Pierce .................... G02C 11/02 |
| 10,070,673 B2 | * | 9/2018 | Mendez ................ G02C 11/12 |

OTHER PUBLICATIONS

Ainsbury et al, "Ionizing radiation induced cataracts: Recent biological and mechanistic developments and perspectives for future research", Mutation Research/Reviews in Mutation Research, vol. 770, No. B, pp. 238-261, Oct.-Dec. 2016.

Carinou et al, "Eye lens monitoring for interventional radiology personnel: dosemeters, calibration and practical aspects of Hp(3) monitoring. A 2015 review", Journal of Radiological Protection, vol. 35, pp. R17-R34, Sep. 7, 2015.

Dauer et al, "Guidance on radiation dose limits for the lens of the eye: overview of the recommendations in NCRP Commentary No. 26", International Journal of Radiation Biology, vol. 93, No. 10, pp. 1015-1023, Apr. 3, 2017.

Domienik et al, "The impact of various protective tools on the dose reduction in the eye lens in an interventional cardiology—clinical study", Journal of Radiological Protection, vol. 36, No. 2, pp. 309, May 16, 2016.

Fetterly et al, "Head and Neck Radiation Dose and Radiation Safety for Intervention Physicians", JACC: Cardiovascular Interventions, vol. 10, No. 5, pp. 520-528, Mar. 13, 2017.

Geber et al, "Eye lens dosimetry for interventional procedures—Relation between the absorbed dose to the lens and dose at measurement positions", Radiation Measurements, vol. 46, No. 11, pp. 1248-1251, Nov. 2011 (Abstract Only).

Jacob et al, "Eye Lens Radiation Exposure to Interventional Cardiologists: A Retrospective Assessment of Cumulative Doses", Radiation Protection Dosimetry, vol. 153, No. 3, pp. 282-293, Jun. 5, 2012.

Kirkwood et al, "Radiation Brain Dose to Vascular Surgeons During Fluoroscopically Guided Interventions Is Not Effectively Reduced by Wearing Lead Equivalent Surgical Caps", J Vasc Surg, vol. 68, No. 2, pp. 567-571, Aug. 2018.

Ko et al, "Health Effects from Occupational Radiation Exposure among Fluoroscopy-Guided Interventional Medical Workers: A Systematic Review", Journal of Vascular and Interventional Radiology, vol. 29, No. 3, pp. 353-366, Mar. 2018.

Meisinger et al, "Radiation Protection for the Fluoroscopy Operator and Staff", American Journal of Roentgenology, vol. 207, No. 4, pp. 745-754, Oct. 2016.

Seals et al, "Cataract Development in Vascular Intervention", Endovascular Today, vol. 15, No. 8, pp. 73-76, Aug. 2016.

Seals et al, "Radiation-Induced Cataractogenesis: A Critical Literature Review for the Interventional Radiologist", CardioVascular and Interventional Radiology, vol. 39, pp. 151-160, Sep. 24, 2015.

Shore, "Radiation and cataract risk: Impact of recent epidemiologic studies on ICRP judgments", Mutation Research/Reviews in Mutation Research, vol. 770, No. B, pp. 231-237, Oct.-Dec. 2016.

Sturchio et al, "Protective Eyewear Selection for Interventional Fluoroscopy", Health Physics, vol. 104, No. 25, pp. 511-516, Feb. 2013.

Van Rooijen et al, "Efficacy of Radiation Safety Glasses in Interventional Radiology", CardioVascular and Interventional Radiology, vol. 37, pp. 1149-1155, Nov. 2, 2013.

Vanhavere et al, "Measurements of eye lens doses in interventional radiology and cardiology: Final results of the ORAMED project", Radiation Measurements, vol. 46, pp. 1243-1247, Aug. 18, 2011.

Vano et al, "Radiation-associated Lens Opacities in Catheterization Personnel: Results of a Survey and Direct Assessments", J Vasc Interv Radiol, vol. 24, pp. 197-204, (2013).

International Preliminary Report on Patentability in International Application No. PCT/US2020/052803, dated Mar. 15, 2022, 8 pages.

Written Opinion of International Searching Authority in International Application No. PCT/US2020/052803, dated Jan. 5, 2021, 7 pages.

International Search Report International Searching Authority in International Application No. PCT/US2020/052803, dated Jan. 5, 2021, 2 pages.

* cited by examiner

MODIFICATION TO LEADED EYEWEAR FOR SIGNIFICANT OPERATOR EYE RADIATION DOSE REDUCTION

PRIORITY

This application is a 371 National Stage of International Application No. PCT/US2020/052803 filed Sep. 25, 2020, which claims the benefit of U.S. Ser. No. 62/907,005, filed Sep. 27, 2019, and U.S. Ser. No. 63/037,813, filed on Jun. 11, 2020, the contents of which are incorporated by reference herein in their entireties.

FIELD

The present disclosure relates to removable eyewear shielding devices, and to methods of use thereof to reduce radiation exposure.

BACKGROUND

Previously described radiation safety eyewear designs include goggle designs, which have lead attenuating material around the lens suctioned to the operator's face to protect the eyes from scatter radiation. These goggles are uncomfortable, heavy, prone to fogging, and limit the field of view of the operator. The suction design, even when vented, results in lens fogging, which limits operator vision. The suction cap is radiopaque and further limits the inferior and lateral fields of view of the operator. These designs have not been commercially developed because of these limitations. Other goggles or eyewear designs provide shielding on all sides including the tops of the eyes. The frames can be made of thick, heavy plastic mixed with metal. These shielding designs can result in fogging and can limit the field of view of the operator. For example, the designs put forth by both Glasser (U.S. Pat. No. 4,021,862) and Janssen (EP3348244) have never gone to market because they are heavy, uncomfortable, result in fogging and limit the field of view of the operator. They are not conducive to clinical practice. Goggles are uncomfortable for short periods and interventionalists that work 12 hours a day 5 days a week in high stress situations will be unlikely to be compliant with this type of design. New types of radiation safety eyewear are needed in the art that provide better protection and comfort with less weight and fogging.

Ocular radiation exposure from fluoroscopically-guided-interventions (FGIs) can cause cataracts. Standard lead eyewear does not significantly reduce eye radiation dose, as the majority of scattered radiation penetrates the operator's eye obliquely. Methods of reducing ocular radiation exposure are needed in the art.

SUMMARY

Provided herein are removable eyewear shielding devices, eyewear comprising a removable eyewear shielding device, and methods of uses thereof for reducing eye radiation exposure, reducing ipsilateral brain radiation exposure, reducing FGI-induced lens opacification, reducing cataract development, and protecting an eye or ipsilateral brain from radiation exposure.

An embodiment provides a removable eyewear shielding device comprising a shielding panel comprising an inferior curved edge 20, a superior curved edge 30, a thin edge 40 joining a first end of the inferior curved edge 20a to a first end of the superior curved edge 30a, and a wide edge 50 joining a second end of the inferior curved edge 20b to a second end of the superior curved edge 30b, wherein the shielding device can be attached to and detached from an eyewear frame comprising a superior lens frame portion 1, an inferior lens frame portion 2, a first lateral lens frame portion 3 joining the inferior lens frame portion 2 to the superior lens frame portion 1 at a hinge 7 side of the eyewear, and a second lateral lens frame portion 4 joining the inferior lens frame portion 2 to the superior lens frame portion 1. The shielding panel can comprise an inferior portion 12, a lateral portion 11, and a nasal bridge portion 13. The inferior curved edge 20 can comprise one or more adhesive strips, one or more inferior conformable wires 21, or a combination thereof, which can extend from a user's nose to a user's upper lateral cheekbone. The wide edge 50 can comprise a slide-on pocket 51, which can be configured to be fastened the shielding device to a temple of the eyewear. An exterior side of the shielding panel can be made of paper or cloth. The shielding panel an comprise a radio-protective material located on an interior side of the shielding panel, or inserted inside a pocket within the shielding panel. The radio-protective material can be a leaded material, or a lead-free metal material. The superior curved edge 30 can comprise one or more superior conformable wires 31. The superior curved edge 30 can comprise one or more adhesive strips. The one or more superior conformable wires 31 can extend from a hinge 7 of eyewear to a thin edge 40, where the one or more inferior conformable wires, the one or more superior conformable wires, or both can be configured to be moldable around and across a user's nose bridge. The shielding panel can be a U-shaped shielding panel. The one or more superior conformable wires can be configured to be moldable along the first lateral lens frame portion 3, the inferior lens frame portion 2, and the second lateral lens frame portion 4 of eyewear. The thin edge 40 can comprise an adhesive piece 41 to fasten the shielding device around a nasal bridge of the eyewear.

Another embodiment provides an eyewear comprising: an eyewear frame comprising a superior lens frame portion 1, an inferior lens frame portion 2, a first lateral lens frame portion 3 joining the inferior lens frame portion 2 to the superior lens frame portion 1 at a hinge 7 side of the eyewear, and a second lateral lens frame portion 4 joining the inferior lens frame portion 2 to the superior lens frame portion 1 at a nasal bridge 5 side of the eyewear; shielding lenses; and a removable eyewear shielding device comprising a U-shaped shielding panel. The removable eyewear shielding device can be attached to the right side of the eyewear frame, to the left side of the eyewear, or to the right side and the left side of the eyewear frame. The eyewear can be safety eyewear or personal eyewear.

An additional embodiment provides a method of reducing eye radiation exposure, reducing ipsilateral brain radiation exposure, reducing FGI-induced lens opacification, reducing cataract development, protecting an eye or ipsilateral brain from radiation exposure, or a combination thereof in a user comprising providing to the user an eyewear comprising an eyewear frame, shielding lenses, and a removable eyewear shielding device comprising a shielding panel, or a removable eyewear shielding device comprising a shielding panel, for use during exposure to ionizing radiation, to reduce the amount of ionizing radiation reaching the user's eye or ipsilateral brain. The shielding device can extend from a first lateral frame of the eyewear to a user's nose, from an inferior frame of the eyewear to a user's lower cheekbone or jaw, and from a second lateral frame and from a temple of the eyewear to a user's upper lateral cheekbone. one or more adhesive strips, one or more inferior conformable wires, or both can be in contact with a user's nose, lower cheekbone or jaw and upper lateral cheekbone to eliminate any space gap between the removable shielding device and the operator's face. The removable eyewear shielding device can protect the eyes and the ipsilateral brain of the user from oblique radiation exposure. A space between a superior frame of the eyewear and a user's face can be open to reduce fogging and to increase a user's comfort.

Another embodiment provides a removable safety eyewear shielding device comprising a left shielding panel, comprising an inferior panel and a lateral panel; a right shielding panel, comprising an inferior panel and a lateral panel; and a nasal bridge shielding panel, wherein each of the left shielding panel, the right shielding panel, and the nasal bridge shielding panel can be individually attached to and detached from any safety eyewear frame. The inferior border of the left shielding panel and the right shielding panel can each have a lip of shielding that extends away from a face of a user to create a shelf at a base of a lower cheek bone and nasal bridge of the user. The left shielding panel, the right shielding panel, and the nasal bridge shielding panel can be made of clear leaded glass, clear lead-attenuated glass, or clear lead attenuating material. The left shielding panel, the right shielding panel, and the nasal bridge shielding panel can be about 0.5 to about 1.0 mm thick clear leaded glass, clear lead-attenuated glass, or clear lead attenuating material. The left shielding panel, the right shielding panel, and the nasal bridge shielding panel can be custom designed to fit an operator's specific facial structure to eliminate any space gap between the shielding panels and the operator's face.

Even another embodiment provides a safety eyewear comprising: an eyewear frame; shielding lenses; and a removable safety eyewear shielding device comprising a removable left shielding panel comprising an inferior panel and a lateral panel; a removable right shielding panel comprising an inferior panel and a lateral panel; and a removable nasal bridge shielding panel, wherein the removable left shielding panel, the removable right shielding panel, and the removable nasal bridge shielding panel can be attached to and detached from lateral and inferior borders of the eyewear frame. The inferior panel of the left and right shielding panels can have a lip of shielding that that extends away from a face of a user to create a shelf at a base of a lower cheek bone and nasal bridge of the user. The left shielding panel, the right shielding panel, and the nasal bridge shielding panel are made of about 0.5 to about 1.0 mm thick clear leaded glass, clear lead-attenuated glass, or clear lead attenuating material. The clear leaded glass, clear lead-attenuated glass, or clear lead attenuating material does not obstruct the field of view of a user. The removable safety eyewear shielding device can be a custom designed shielding device molded to an operator's face to eliminate any space gap between the removable left shielding panel, the removable right shielding panel, the removable nasal bridge shielding panel and the operator's face. The removable safety eyewear shielding device can protect the eyes of a user from radiation exposure. The removable left shielding panel and the removable right shielding panel can be worn concurrently or individually to lighten the eyewear, and wherein an unworn shielding panel can be easily stored. The superior border of the safety eyewear can be open to reduce fogging and to increase a user's comfort. The eyewear shielding device can protect the eyes of the operator from oblique radiation exposure.

Another embodiment provides a method of reducing eye radiation exposure, reducing FGI-induced lens opacification, reducing cataract development, or a combination thereof comprising providing any of the safety eyewear or the removable safety eyewear shielding devices described herein to a user for use during expose to ionizing radiation such that the amount of ionizing radiation reaching the user's eyes is reduced.

Yet another embodiment provides a method of generating removable safety eyewear shielding device having a custom designed fit based on specific contours of a user's face. The method can comprise determining the user's specific facial structure pattern using three dimensional scanning; creating a three dimensional scanned model of the user's facial structure pattern; translating the facial structure pattern into a mold of a left shielding panel comprising an inferior panel and a lateral panel; a right shielding panel comprising an inferior panel and a lateral panel; and a nasal bridge shielding panel; and casting the safety eyewear shielding device into a clear leaded glass, clear lead-attenuated glass, or clear lead attenuating material; thereby generating a removable safety eyewear shielding device that is specific to the user's face. The removable safety eyewear shielding device can be attached to and detached from a safety eyewear frame.

An inferior border of each of the left shielding and the right shielding panel can have a lip of shielding that that extends away from a face of a user to create a shelf at a base of a lower cheek bone and nasal bridge of the user. The mold can be a silicone medium that can be further customized for finer aspects of facial contouring.

DETAILED DESCRIPTION

Figure 1:
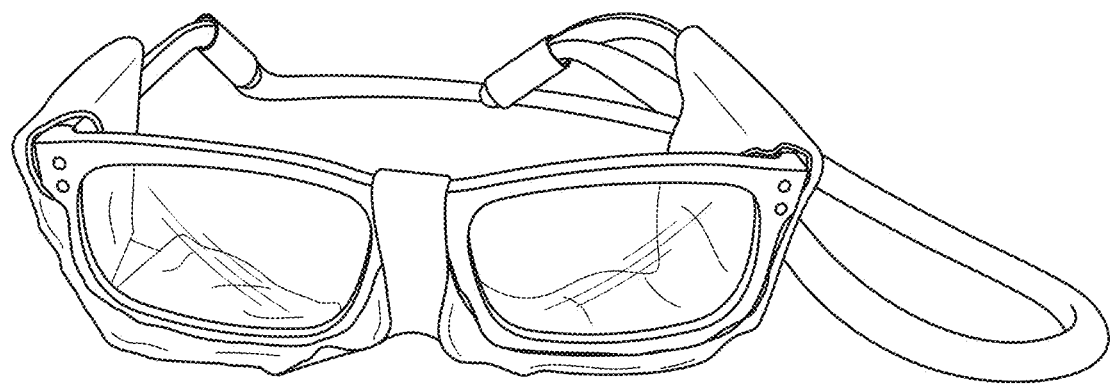
FIG. 1 illustrates a modified eyewear design with covered lead-sheeting attached to the lateral and inferior glasses' frame.

The lens of the eye is one of the most radiosensitive tissues in the human body; exposure to ionizing radiation is known to cause posterior lens opacification and cataracts.[1,2] Understanding the impact of these lens changes on individuals who perform fluoroscopically-guided interventions (FGIs) or other procedures involving ionization radiation exposure has become increasingly important. A recent systematic review including 34 studies reported that up to 80% of interventionalists have radiation-related lens changes on ophthalmic examination, indicating a need for greater emphasis on radiation protection.[3-6,17]

Commercially available leaded eyewear does not decrease corneal or lens dose to interventionalists. This is because the majority of radiation to an operator's eyes is not from direct X-rays hitting the eye at a 90 degree angle but from oblique radiation that scatters in all directions from the patient. The operator's eye closest to the X-ray source is the eye with the highest dose. For example, when an operator stands on the right side of the patient with the C arm (fluoroscopy unit, see FIG. 6) on the left side, the operator's left eye is the eye with the most exposure. In this configuration the operator's right eye dose is 48% of the left eye dose. In an embodiment leaded eyewear was enhanced with leaded shielding molded to the face of the operator to include inferior, nasal bridge and lateral face protection bilaterally. This modification decreased left eye radiation dose by 85% and decreased left sided brain radiation dose by 41%. There was no significant decrease in radiation dose to the right eye from any eyewear model including this modification. That is because the majority of radiation to the operator's right eye (furthest eye from the X-ray source) is coming from scatter radiation already attenuated through the facial bones. Protecting the eye closest to the radiation source is possible with additional protective shielding. If the fluoroscopy set up changes for a particular procedure (e.g., FGI with the operator on the left side of the patient and fluoroscopy unit on the right side of the patient) then it is the operators right eye with the highest dose that can be protected with the devices. If the shielding does not fit the form of the operator's face then it does not offer any protection.

Disposable Removable Safety or Personal Eyewear Shielding Device

An embodiment provides a novel modification to leaded eyewear that is lightweight, detachable, and optionally disposable. The device conforms to the operator's face to offer radiation protection to the eye closest to the X-ray source and significant ipsilateral brain protection without causing fogging or limiting the field of view of the operator (see e.g., FIGS. 7-8 and 10-12).

A removable shielding device can be made of radioprotective material, such as a leaded or lead free metal shielding panel that is lightweight and radio-protective. Non-limiting examples of radioprotective material include, for example, non-lead and lead free shielding (e.g. RADPAD™ material, RADPAD Worldwide Innovations & Technologies, Lenexa, Kan.). These materials can be made of additives and binders mixed with attenuating heavy metals similar to lead that absorb or block radiation (e.g., tin, antimony, tungsten, bismuth, or other elements). Flexible lead vinyl sheets and lead composite shielding, which is a mixture of lead and other lighter weight metals that attenuate radiation (e.g. tin, rubber, PVC vinyl, etc.) can also be used. Other examples of suitable radioprotective materials are described in, for example, US Pat. Publ. 20060230495, US Pat. Publ. 20060151750, and US Pat. Publ. 20180271610.

In an embodiment, the radioprotective material can be inserted into a pocketed material (e.g., paper or cloth) making up a removable shielding device. In another embodiment, the radioprotective material can comprise a lining located on the inside (interior or on the side touching a user's face), on the outside (exterior or on the side facing outwards), or both on the inside and on the outside of the removable paper or cloth shielding device. A removable shielding device can be molded along an eyewear frame, and extend from a user's nose, lower cheekbone (or lower, for example, to the jaw bone), and upper cheekbone to eliminate any space gap between the removable shielding device and the operator's face. The removable shielding device, although disposable, can be re-wearable, lightweight, comfortable and effective at significantly reducing radiation to the eye covered and the ipsilateral brain of the user.

Figure 6:
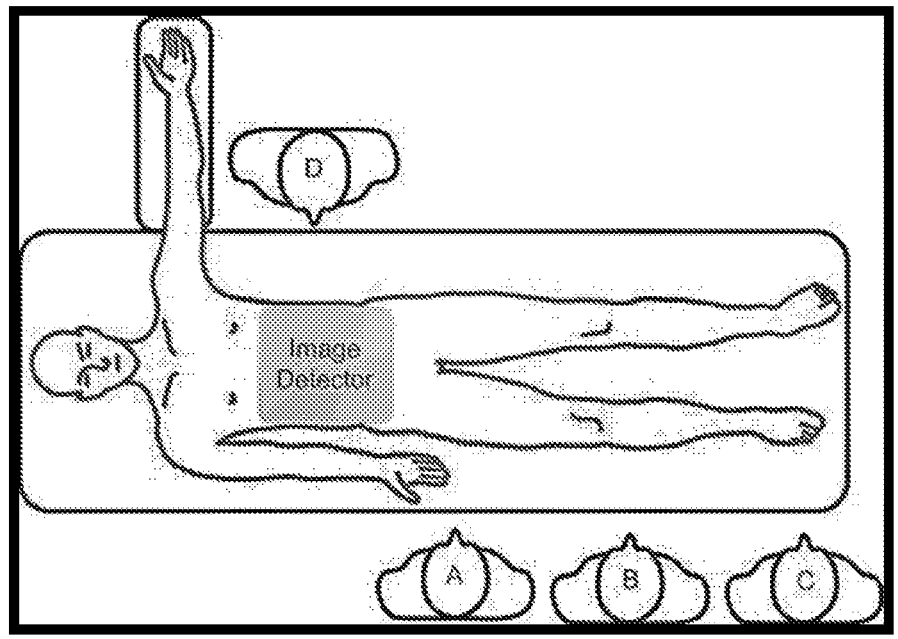
FIG. 6 illustrates the radiation exposure risk of a user based on the localization of the radiation source.

Since only the radiation dose of the eye closest to the X-ray source is decreased by additional shielding, the disposable design can be attached to only one side of the eyewear frame (see FIGS. 9 and 13-15), and the side can be changed based on the orientation of the procedure (see FIG. 6). That is, a removable shielding device can be designed to fit the left frame or right frame of eyewear. This significantly lightens the weight and increases comfort and usability of the device. A removable shielding device can be a right sided or a left sided attachment, offering protection to whichever eye is closest to the X-ray source no matter what the operating room orientation is. In an embodiment, the shield can be reversable so that it can be worn on the left frame or the right frame, for example, by reversing the side facing the wearer to be the side facing away from the wearer. The removable shielding device does not require any suction application, and the superior border of the eyewear can remain open, which can prevent the formation of fogging and condensation.

One or more adhesive strips, one or more inferior conformable wires, or more superior conformable wires, or combinations thereof can eliminate the air gap between the lens of the glasses and the operator's face, obscuring scattered X-rays, while achieving a comfortable, lightweight fit with no significant visual impairment. The removable shielding device can be universally compatible with all types of eyewear (e.g., safety eyewear or personal prescription glasses) as it can slip over the glasses frame and contour to the operator's face using one or more adhesive strips and/or one or more conformable wires.

Figure 10:
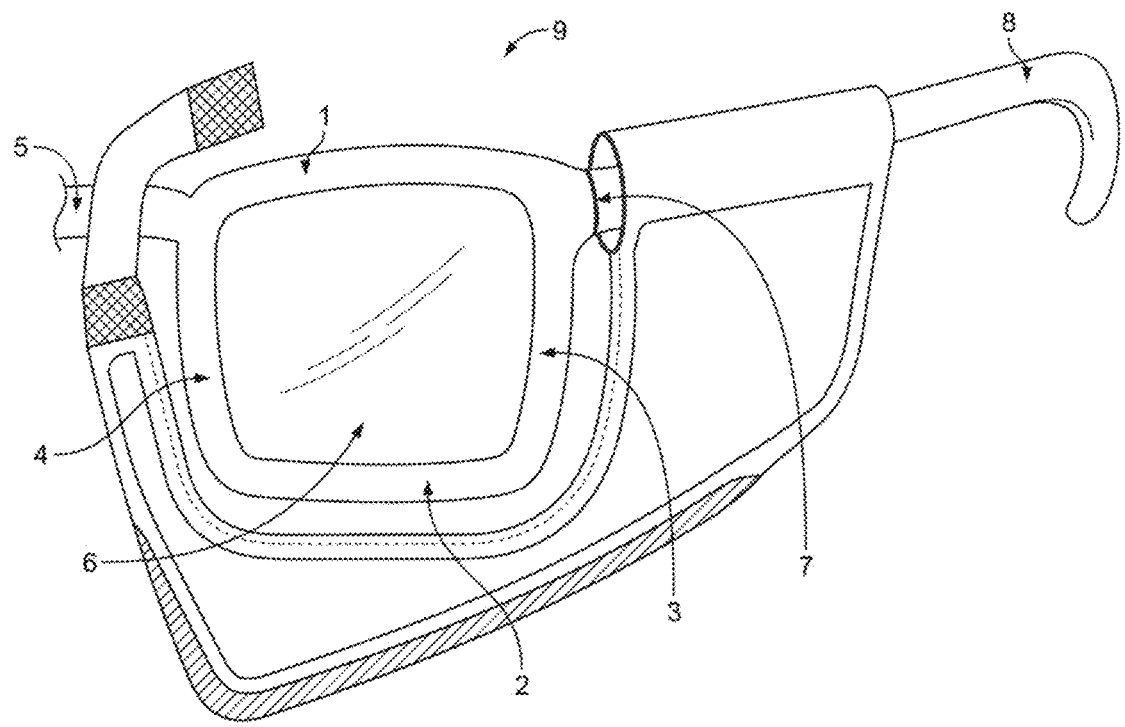
FIG. 10 is a representation of a removable eyewear with a U-shaped shielding device attached to an eyewear frame. 1: superior lens frame portion; 2: inferior lens frame portion; 3: first lateral lens frame portion; 4: second lateral lens frame portion; 5: nasal bridge; 6: lens; 7: hinge; 8: temple; 9: superior border.

As illustrated in, for example, FIG. 10, a removable eyewear shielding device can be attached to or detached from any eyewear comprising a superior lens frame portion 1, an inferior lens frame portion 2, a first lateral lens frame portion 3 joining the inferior lens frame portion 2 to the superior lens frame portion 1 at a hinge 7 side of the eyewear (i.e., a first lateral lens frame can face the outside of an eyewear, away from a user's face), and a second lateral lens frame portion 4 joining the inferior lens frame portion 2 to the superior lens frame portion 1 at a nasal bridge 5 side of the eyewear (i.e., a second lateral lens frame can face the inside of an eyewear, by a user's nose). While a lens frame is shown in the figures as a generally rectangular shape, a shielding device can fit any lens frame shape, for example, round, square, oval, etc.

FIG. 10 illustrates a removable shielding device attached to a left side of an eyewear. As discussed below, a removable shielding device can also be attached to a right side of an eyewear, that mirrors a left side of an eyewear. Therefore, a shielding device attached to a right side of an eyewear can be described as a mirror of a shielding device attached to a left side of an eyewear. For example, a right side of an eyewear can comprise a superior lens frame portion, an inferior lens frame portion, a first lateral lens frame portion joining the inferior lens frame portion to the superior lens frame portion at a hinge side of the eyewear (i.e., a right hinge of an eyewear), and a second lateral lens frame portion joining the inferior lens frame portion to the superior lens frame portion at a nasal bridge side of the eyewear (i.e., a right side of a nasal bridge of an eyewear).

Figure 7:
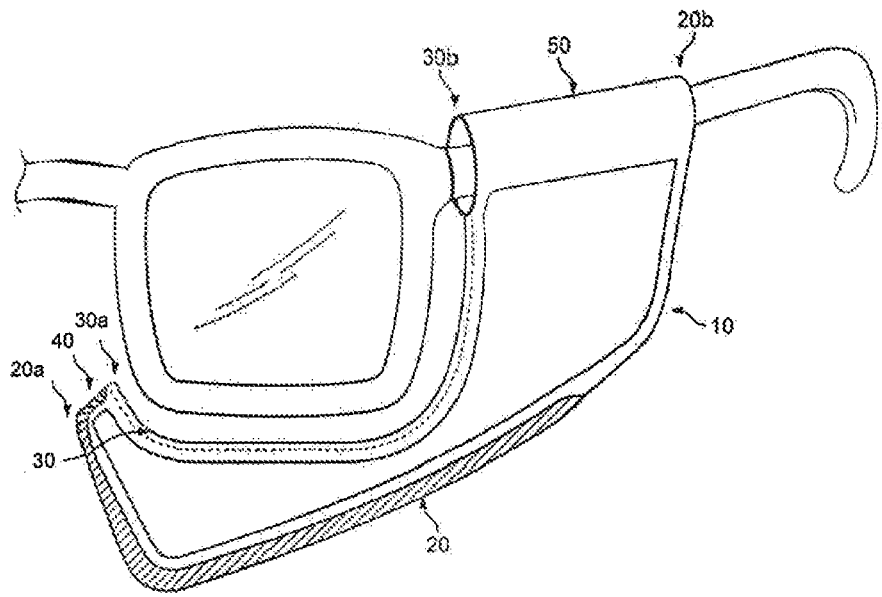
FIG. 7 is a representation of the different parts of a removable eyewear shielding device attached to an eyewear frame. 10: U-shaped shielding panel; 20: inferior curved edge; 20a: first end of the inferior curved edge; 20b: second end of the inferior curved edge; 30: superior curved edge; 30a: first end of the superior curved edge; 30b: second end of the superior curved edge; 40: thin edge; 50: wide edge.
Figure 8:
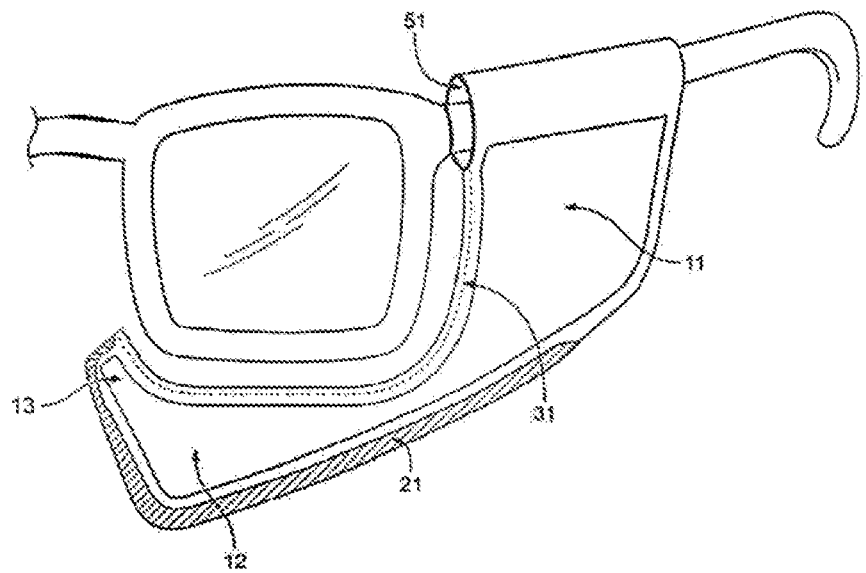
FIG. 8 is a representation of the different parts of a removable eyewear shielding device attached to an eyewear frame. 11: lateral portion of the shielding panel; 12: inferior portion of the shielding panel; 13: nasal bridge portion of the shielding panel; 21: adhesive strip and inferior conformable wire; 31: superior conformable wire; 51: slide-on pocket.

As illustrated in FIGS. 7 and 8, a removable eyewear shielding device can comprise a shielding panel comprising an inferior curved edge 20, a superior curved edge 30, a thin edge 40 joining a first end of the inferior curved edge 20a to a first end of the superior curved edge 30a, and a wide edge 50 joining a second end of the inferior curved edge 20b to a second end of the superior curved edge 30b.

In an embodiment, an inferior curved edge can range from about 10 centimeters to about 15 centimeters (e.g., about 10, 11, 12, 13, 14, or 15 cm or any range or value between about 10 cm and about 15 cm); a superior curved edge can range from about 8 centimeters to about 12 centimeters (e.g., about 8, 9, 10, 11, 12 cm or any range or value between about 8 cm and about 12 cm); a thin edge can range from about 5 millimeters to about 2 centimeters (e.g., about 5, 6, 7, 8, 9, 10, 12, 15, 18, 20 mm or any range or value between about 2 mm and about 20 mm); and a wide edge can range from about 2 centimeters to about 9 centimeters (e.g., about 2, 3, 4, 5, 6, 7, 8, 9 cm or any range or value between about 2 cm and about 9 cm).

As illustrated in FIG. 8 shielding panel can comprise an inferior portion 12, a lateral portion 11, and a nasal bridge portion 13.

Figure 11:
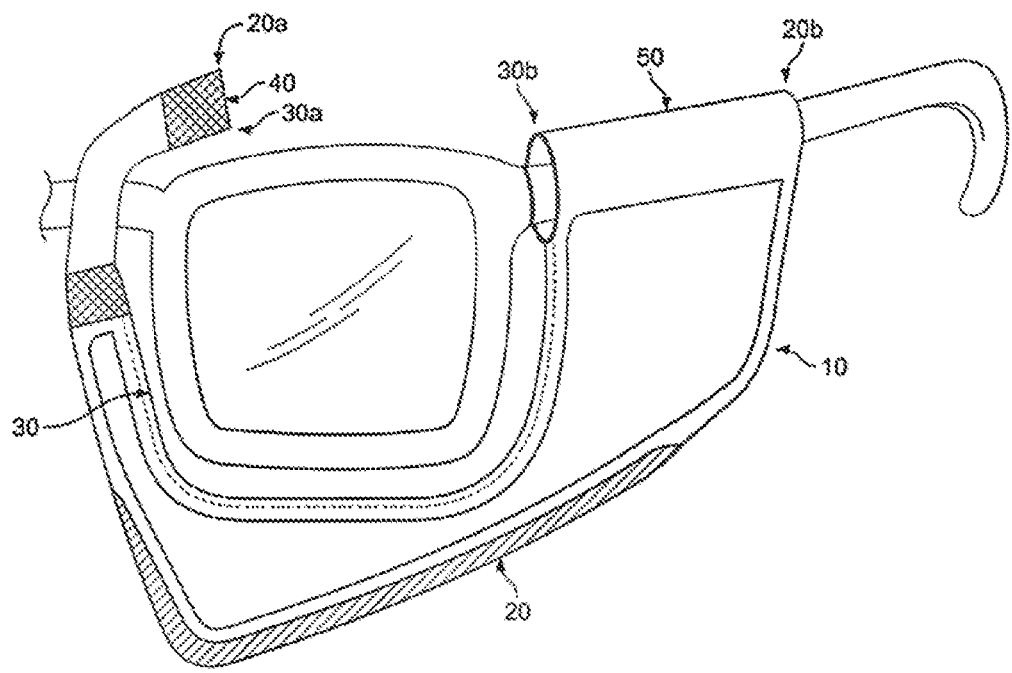
FIG. 11 is a representation of the different parts of a removable eyewear with a U-shaped shielding device attached to an eyewear frame. 10: U-shaped shielding panel; 20: inferior curved edge; 20a: first end of the inferior curved edge; 20b: second end of the inferior curved edge; 30: superior curved edge; 30a: first end of the superior curved edge; 30b: second end of the superior curved edge; 40: thin edge; 50: wide edge.
Figure 12:
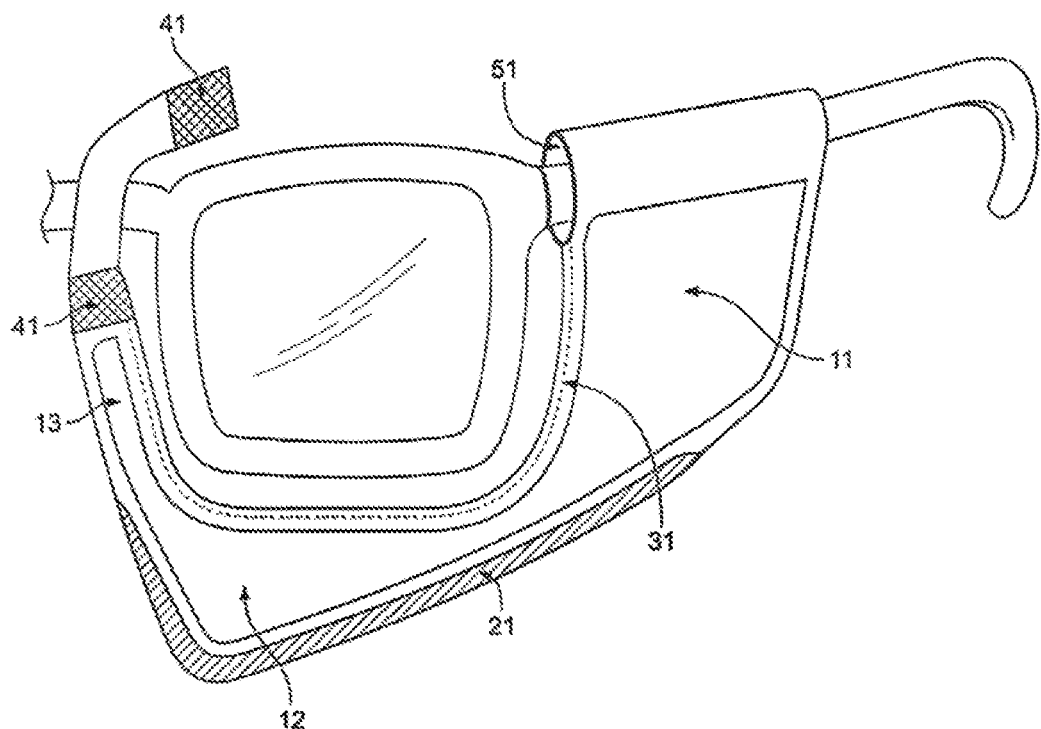
FIG. 12 is a representation of the different parts of a removable eyewear with a U-shaped shielding device attached to an eyewear frame. 11: lateral portion of the shielding panel; 12: inferior portion of the shielding panel; 13: nasal bridge portion of the shielding panel; 21: adhesive strip and inferior conformable wire; 31: superior conformable wire; 41: adhesive piece; 51: slide-on pocket.
Figure 13:
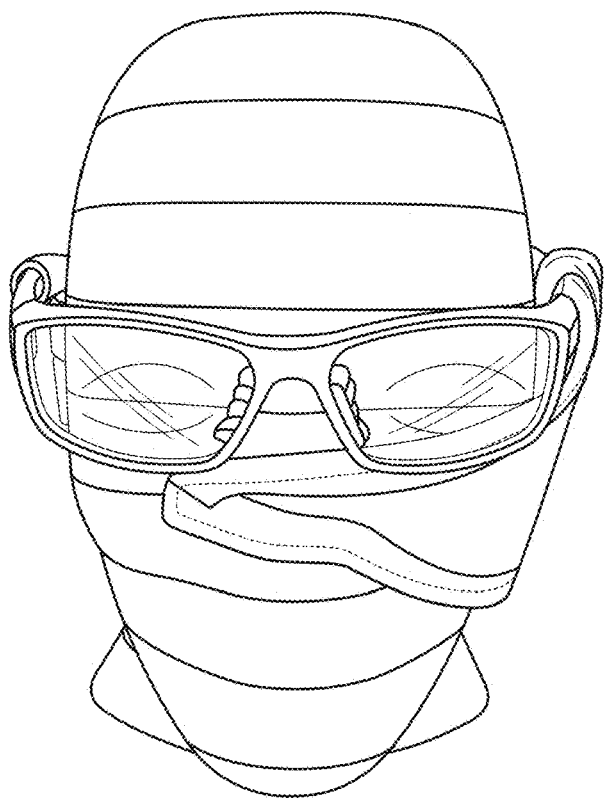
FIG. 13 illustrates a front view of a modified eyewear design with a removable eyewear shielding device attached to an eyewear frame and molded on a user's nose.
Figure 14:
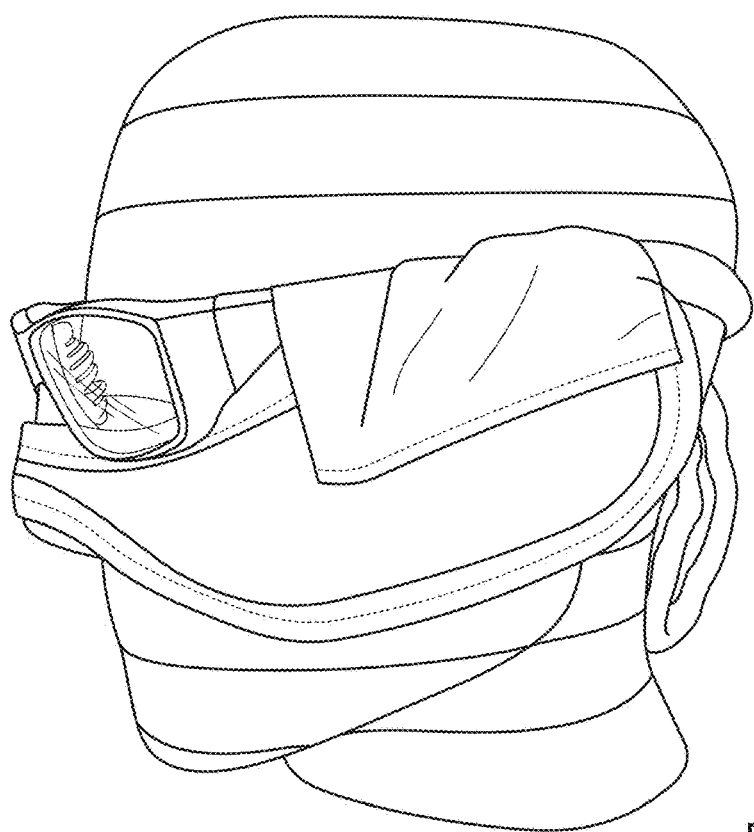
FIG. 14 illustrates a left-side view of a modified eyewear design with a removable eyewear shielding device attached to an eyewear frame and molded on a user's nose.
Figure 15:
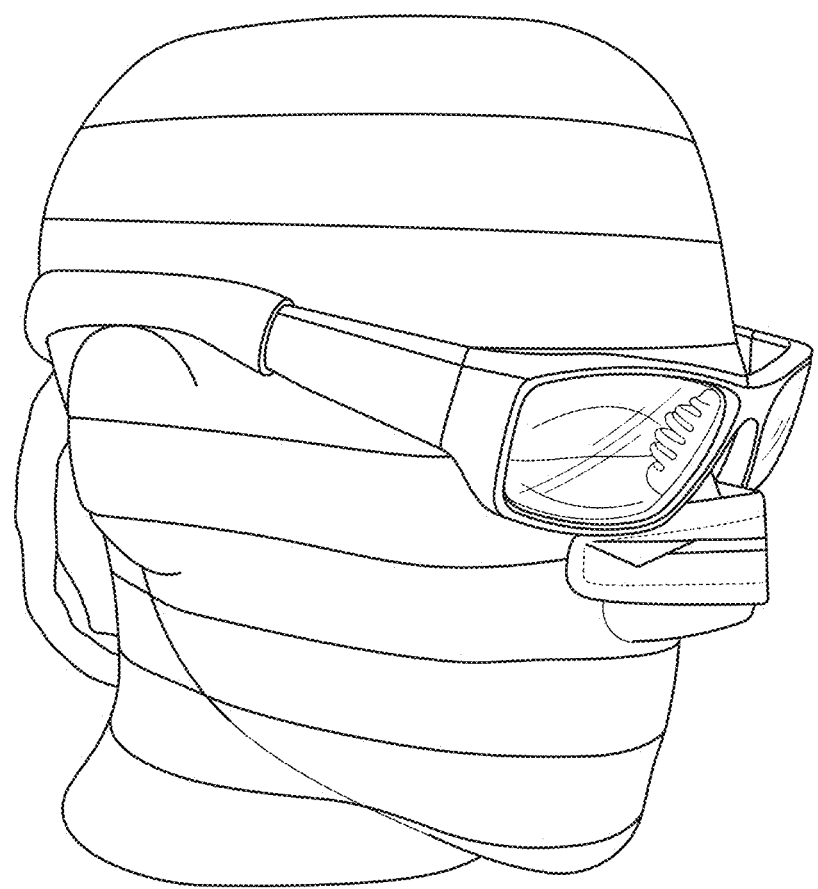
FIG. 15 illustrates a right-side view of a modified eyewear design with a removable eyewear shielding device attached to an eyewear frame and molded on a user's nose.

As further illustrated in FIGS. 11 and 12, a removable eyewear shielding device can comprise a generally U-shaped shielding panel that extends along a second lateral lens frame portion 4 of the eyewear, and a nasal bridge 5.

An inferior portion of a shielding panel can extend from an inferior frame of an eyewear to a user's lower cheekbone (or lower, e.g. to a user's jaw bone); a lateral portion of a shielding panel can extend from a first lateral frame of an eyewear (i.e., a lateral frame facing outward of an eyewear, away from a user's face) and from a temple of an eyewear to a user's upper lateral cheekbone; and a nasal bridge portion of a shielding panel can extend from a second lateral frame of an eyewear (i.e., a lateral frame facing inward of an eyewear, by a user's nose) to a user's nose. In an embodiment, the inferior portion of a shielding panel can extend from an inferior frame of an eyewear to a user's lower cheekbone so that it contacts a mask worn over the wearer's nose and mouth. In an embodiment the inferior portion of a shielding panel extending from an inferior frame of an eyewear to a user's lower cheekbone can attach to a mask worn over the wearer's nose and mouth by one or more clips, hook-and-loop fasteners, hook-and-pile fasteners, touch fasteners, or adhesives located on the mask or inferior portion of the shielding panel. That is, a shielding device described herein can be used to provide protection of the eyes of a user and also to the face and head of a user. For example, and as further detailed in Example 2, the shielding device can cover the upper ipsilateral face of a user, which allow the device to protect the brain of the user as well as the eyes. As used herein, the term "eyewear shielding device" is meant to refer to the fact the shielding device is attached to an eyewear, but should not be understood as a means to protect only the eyes of a user. In fact, eyewear shielding devices can protect the eyes, face, and head of a user.

Inferior, lateral, and nasal bridge portions of the device can be made of radioprotective material, such as a leaded or lead-free metal shielding panel that is lightweight and radioprotective. A radioprotective material can be inserted into a pocketed material, or can comprise a lining covering the inside (internal or on the side touching a user's face), the outside (external or on the side facing outwards), or both the inside and the outside of the shielding panel. A pocketed material and a lining material can be made of, for example, soft paper or cloth.

An inferior curved edge 20 can comprise one or more adhesive strips, which can extend from a nasal bridge portion of a shielding device (i.e., by a user's nose) along an inferior portion of a shielding device (i.e., along a user's lower cheekbone or jawbone) and to a lateral portion of a shielding device (i.e., along a user's upper lateral cheekbone). A superior curved edge 30 can also comprise one or more adhesive strips at any portion along the superior curved edge.

In an embodiment, an adhesive strip can be located within the edge of an inferior curved edge of a shielding device, so that an adhesive strip can contact a user's skin independently of the side of an eyewear to which the shielding device is attached.

In another embodiment, one or more adhesive strips can be located on an inside face of a shielding device. For example, the device can comprise 1, 2, 3, or more rows of adhesive strips to maximize adhesion of a device to a user's skin.

One or more adhesive strips can be continuous along the entire length of the inferior curved edge (i.e., from a nasal bridge portion of a shielding device, along an inferior portion of a shielding device and to a lateral portion of a shielding device), or the superior curved edge, or both edges. In another embodiment, one or more adhesive strips can be discontinuous along the inferior curved edge and superior curved edge. For example, an inferior curved edge of a nasal bridge portion of a shielding device can comprise a first series of one or more adhesive strips, an inferior curved edge of an inferior portion of a shielding device can comprise a second series of one or more adhesive strips, and an inferior curved edge of a lateral portion of a shielding device can comprise a third series of one or more adhesive strips.

An adhesive strip can be made of any material that can be applied on the skin, and that provides good adhesion to a user's skin. An adhesive strip is easily detachable from a user's skin. An adhesive strip can be, for example, made of medical tape, adhesive silicone, bandage-type adhesive material (such as an acrylate, including methacrylates and epoxy diacrylates), or any other suitable adhesive.

An inferior curved edge 20 and a superior curved edge 30 can comprise one or more inferior conformable wires 21, one or more superior conformable wires 31, or both one or more inferior and one or more superior conformable wires.

In an embodiment, a conformable wire can be located within the edge of an inferior curved edge and/or within the edge of a superior curved edge of a shielding device. Alternatively, one or more conformable wires can be located on one of the faces of device (i.e., on the inside of the device or on the outside of the device). As shown in FIGS. 7-8 and 10-12), in an illustrative embodiment, one or more conformable wires can be located, for example, on the inside of the device, on the side facing a user's face (see dotted line in FIGS. 7-8 and 10-12)

A conformable wire can be made of any material that is flexible enough to allow the conformable wire to be molded along an eyewear frame (along a first lateral lens frame portion 3, an inferior lens frame portion 2, and an second lateral lens frame portion 4, extending from a hinge 7 of the eyewear to a nasal bridge), and along a user's face (from a user's nose to a user's upper lateral cheekbone), and rigid enough for the molded wire to stay in place. For example, a conformable wire can be a thin aluminum wire, a thin aluminum plate, a flat aluminum strip, or any other suitable material.

In one embodiment, a superior conformable wire can extend from a hinge 7 of the eyewear to a user's nose, where the inferior conformable wire and/or the superior conformable wire can be molded around and across a user's nose bridge. One or more conformable wires, one or more adhesive strips, or combinations thereof can provide support for the shielding device to be held on a user's nose (see FIGS. 13-15).

In an additional embodiment, a removable eyewear shielding device can be designed to fit on a user's nose, that is instead of being fastened to an eyewear nasal bridge, it is molded over the user's nose. A conformable wire can be used to mold the shielding panel over a user's nose so that the shielding panel can rest in place by being held by a user's nose. In this conformation, there is no need for the shielding device to be fastened to the nasal bridge of an eyewear.

In an embodiment, an inferior conformable wire can extend from a user's nose to a user's upper lateral cheekbone, and be molded around and across a user's nose bridge. In another embodiment, a superior conformable wire can extend from a hinge 7 of the eyewear to a user's nose and be molded around and across a user's nose bridge. In an additional embodiment, both an inferior conformable wire and a superior conformable can extend from a user's nose to a user's upper lateral cheekbone, and from a hinge 7 of the eyewear to a user's nose, respectively, and be molded around and across a user's nose bridge to ensure a stronger holding of the shielding device on a user's nose. See, e.g., FIG. 8.

Figure 9:
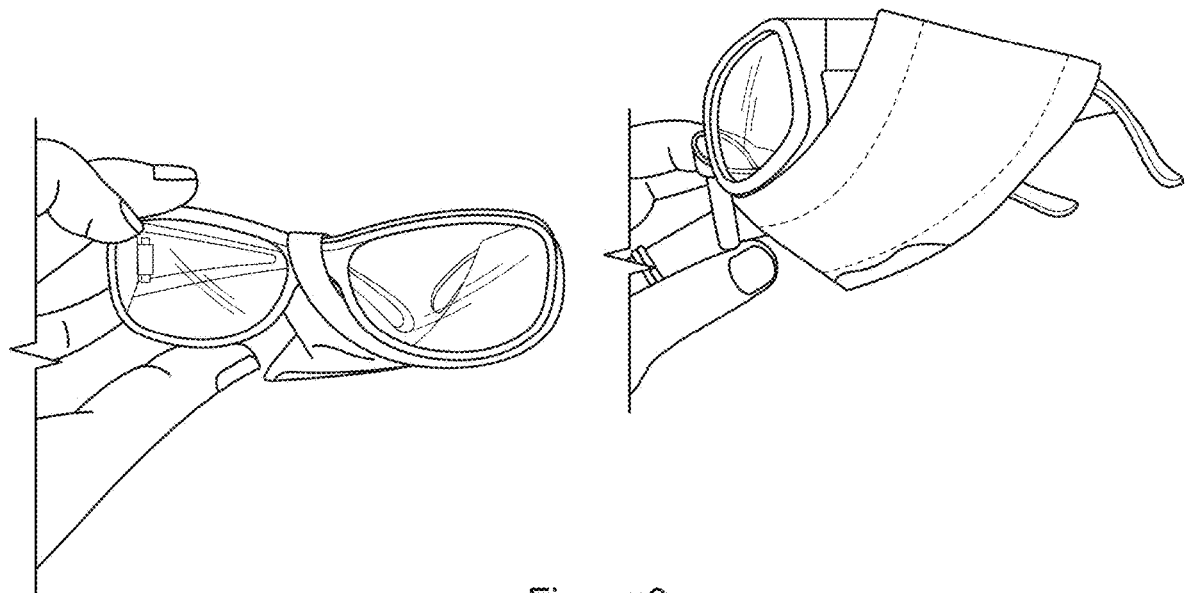
FIG. 9 illustrates a modified eyewear design with a removable eyewear shielding device attached to an eyewear frame.

In another embodiment, where the shielding panel can be, for example, a U-shaped shielding panel, a superior conformable wire 31 which can extend from a hinge 7 of the eyewear to a nasal bridge of the eyewear (see FIG. 9). A thin edge 40 of a shielding device can comprise one, two, or more adhesive pieces 41 to fasten a shielding device around a nasal bridge of an eyewear. As shown in FIGS. 10-12, when a shielding device is slid on a temple of an eyewear, a gap can be present between a superior curved edge of a device (30) and a frame of an eyewear (i.e., an inferior lens frame portion 2, a first lateral lens frame portion 3, and a second lateral lens frame portion 4). By fastening a shielding device to an eyewear, through the attachment of a thin edge (40) around a nasal bridge of an eyewear, an adhesive piece can be used to tighten a shielding device around an eyewear frame to reduce or eliminate a gap between a shielding device and an eyewear. Any gap can further be reduced or eliminated using conformable wires or adhesive strips present on the shielding device.

An adhesive piece can be, for example a piece of tape, bandage-type adhesive material, or medical tape. An adhesive piece can have various shapes; for example an adhesive piece can be a square adhesive piece (as shown in an illustrative embodiment illustrated in FIGS. 10-12), a round shape, a rectangular shape, a triangular shape, or any other suitable shape that allow an adhesive piece to fasten a shielding device to an eyewear. Alternatively, an adhesive piece can comprise two portions, that can be contacted with one another to securely fasten a device to an eyewear. For example, an adhesive piece can be a hook-and-loop fastener, a hook-and-pile fastener or a touch fastener; where a first portion can comprise hooks, and a second portion can comprise loops, so that upon contacting of the hooks with the loops, two portions can be fasten to one another. A first portion of an adhesive piece can be located at an edge of a thin edge, and a second portion can be located at a distance from an edge of a thin edge, so that an thin edge can be wrapped around a nasal bridge of an eyewear and a thin edge comprising first portion of an adhesive piece can be fasten to a second portion of an adhesive piece (see FIG. 12). A first and a second portion of an adhesive piece can range, for example, from about 0.5 centimeters to about 6 centimeters (e.g., about 0.5, 1.0, 2.0, 3.0, 4.0, 5.0, 6.0 cm or any range or value between about 0.5 cm and about 6 cm), so that a shielding device can be properly adjusted to an eyewear to minimize any gap between a shielding device and an eyewear frame.

A wide edge 50 can comprise a slide-on pocket 51 such that a temple 8 of an eyewear can slide into a slide-on pocket to fasten a shielding device to a temple of an eyewear. A radioprotective material can be inserted into a pocketed material made of paper or cloth to make up the removable shielding device; or as a lining located on the inside (on the side touching a user's face), on the outside (on the side facing outwards), or both on the inside and on the outside of the radioprotective material can be used to make up the removable shielding device. In an embodiment, a pocketed material, or alternatively, a lining material (either located inside, outside or both inside and outside of the radioprotective material) can be folded at a wide edge of the shielding device, so that a temple of an eyewear can be slid into the pocket.

A slide-on pocket can extend along the entire length of a wide edge of a shielding device, and can range from about 2 centimeters to about 6 centimeters in length (e.g., about 2, 3, 4, 5, 6 cm or any range or value between about 2 cm and about 6 cm). A slide-on pocket can be wide enough so that any temple of any eyewear can be slid through the pocket. For example, a slide-on pocket can range from about 1 centimeter to about 2 centimeters (e.g., about 1, 1.25, 1.5, 1.75, 2 cm or any range or value between about 1 cm and about 2 cm) in width.

In an embodiment, a removable shielding device can be designed to fit both the left frame and the right frame of an eyewear. Due to the flexibility of the material comprising the removable shielding device (i.e., flexible radioprotective panels, soft paper or cloth, conformable wires, and adhesive strips), a removable shielding device can be attached to and molded to a left frame of an eyewear or to a right frame of an eyewear, interchangeably. For example, to provide radiation protection to a left eye of a user, a removable shielding device can slide onto a left temple of an eyewear and be fastened to a left side of a nasal bridge of the eyewear. Alternatively, and to provide protection to a right eye of a user, the removable shielding device can slide onto a right temple of an eyewear and fastened to a right side of a nasal bridge of the eyewear.

In an embodiment, shielding devices can be specifically designed to slide onto the right or left temple.

In an embodiment, two removable shielding devices can be worn together on an eyewear, to prevent a user from being exposed to harmful radiation if a user moves during the course of a procedure. For example, if a user moves from a position A, B, or C (as illustrated in FIG. 6) to a position D, it could result in a user having an unexposed eye protected and an exposed eye unprotected. In such case, when a user can be required to move during a procedure, a first removable shielding device can be attached to a left frame of an eyewear, and a second removable shielding device can be attached to a right frame of an eyewear. A first removable shielding device can slide onto a left temple of an eyewear and be fastened to a left side of a nasal bridge of the eyewear, while a second removable shielding device can slide onto a right temple of an eyewear and be fastened to a right side of a nasal bridge of the eyewear. Wearing both devices can prevent a user from interrupting a procedure to switch from a removable device attached to one side (i.e., left side or right side) to the other side (i.e., right side or left side).

Alternatively, a nasal bridge panel can be one piece connecting an inferior and a lateral portion of a left removable shielding device and an inferior and a lateral portion of right removable shielding device into one removable shielding device covering both a left side and a right side of an eyewear. A one piece nasal bridge panel can extend from a left inferior lens frame portion to a left side of a nasal bridge (i.e., along a left second lateral lens frame portion), along a nasal bridge, and from a right side of a nasal bridge to a right inferior lens frame portion (i.e., along a right second lateral lens frame portion); and be fasten to a nasal bridge of an eyewear.

Custom Designed Removable Safety or Personal Eyewear Shielding Device

In an embodiment a leaded eyewear device can be custom made from the facial contour of an operator (see e.g., FIG. 1). The shielding portion of the device can be made of clear leaded glass, clear lead-attenuated glass, or clear lead attenuating material, which does not obstruct the operators field of view with dense radiopaque material and can be detachable so that only the eye closest to the X-ray tube is protected. The resulting device is light-weight, comfortable, and does not cause fogging or limit field of view.

Each interventionalist has different facial geometry and therefore custom made eyewear can fully protect the eye of the operator. In one embodiment, custom designed fit devices based on the contour of the operator's face is provided herein. A custom fit can be achieved by computer aided manufacturing, rapid prototyping and three dimensional (3D) printing that can create a 3D scanned model of the operator's facial structure. Once completed this pattern can be translated to a mold that closes the gap between the operators face and the eyewear. Finer aspects of facial contouring can be customized through a silicone medium that can then be cast into a leaded or lead equivalent material. In another embodiment, non-custom fit devices are provided herein, which are similar to the custom fit version. In this embodiment, several sizes of devices are manufactured and a user can choose the best fit.

The device is light weight, detachable from the operators current leaded glasses, and easily stored. This allows only one eye side (i.e., left or right side) to be worn to lighten the design and increase comfort and usability. Fogging does not occur because there is no suction application. Casting into a clear medium further limits any reduction in an operators field of view. The inferior aspect of the attachment can have a lip of shielding that comes off the face for a few millimeters to create a shelf at the base of the lower cheek bone and nasal bridge to deflect additional X-rays. The custom design eliminates the space gap between the eye of the operator and the face while achieving a comfortable, light weight fit with no visual impairment.

Present technology consists of eyewear that only has leaded lenses added to a routine frame, which do not provide adequate radiation dose reduction to the operators eye. The compositions and methods provided herein can reduce radiation to the operator's eye closest to the X-ray tube by >80%. This is an enormous operator safety benefit, ensuring that interventionalists can treat patients without exceeding the International Commission on Radiological Protection (ICRP) ocular dose thresholds. Since the design is individually detachable from each lens of the leaded glasses, if the room geometry changes (operator is on the left side of the patient with the fluoroscopy unit on the right side), then the glasses can be quickly adjusted.

The ICRP demands that interventionalists limit ocular (lens) radiation exposure to 20 mSv a year averaged over 5 years with no single year exceeding 50 mSv. It is estimated that up to 60% of operators exceed the 20 mSv/year lens exposure limit. Currently available leaded eyewear (that is universally worn by all interventional radiologists, cardiologists, neurosurgeons as well as vascular surgeons throughout the world) offers no ocular protection.

As illustrated in FIG. 1, a custom designed removable safety or personal eyewear shielding device can comprise a left shielding panel, comprising an inferior panel and a lateral panel; a right shielding panel, comprising an inferior panel and a lateral panel; and a nasal bridge shielding panel. A non-custom designed removable safety or personal eyewear shielding device can comprise the same elements as a custom designed device.

A left shielding panel, a right shielding panel, and a nasal bridge shielding panel can be made any material than can be radioprotective. In one embodiment, the left shielding panel, right shielding panel, and nasal bridge shielding panel can be made of clear leaded glass, clear lead-attenuated glass, or clear lead attenuating material. For example, shielding panels (i.e., a left shielding panel, a right shielding panel and a nasal bridge shielding panel) can be about 0.5 to about 1.0 mm thick clear leaded glass, clear lead-attenuated glass, or clear lead attenuating material.

Shielding panels can comprise a lip of shielding that can extends away from a face of a user to create a shelf at a base of a lower cheek bone and nasal bridge of a user. In an embodiment, shielding panels can be custom designed to fit an operator's specific facial structure to eliminate any space gap between the shielding panels and the operator's face.

To provide for lighter and more comfortable eyewear, the shielding panels can be individually attached to and detached from a safety or personal eyewear frame, such that a safety or personal eyewear comprises a left shielding panel alone, a right shielding panel alone, a right shielding panel or a left shielding panel and a nasal bridge shielding panel, or a left shielding panel, a right shielding panel and a nasal bridge shielding panel.

The compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

The following are provided for exemplification purposes only and are not intended to limit the scope of the embodiments described in broad terms above.

EXAMPLES

Example 1: Phantom and Clinical Studies

Two experiments were performed in this study. The first was a controlled phantom study to assess the corneal and lens doses of both eyes received by the operator when wearing different protective eyewear during a simulated FGI. The second was a single center, prospective study of left eye dose reductions to the operator when wearing standard lead eyewear and the eyewear design shown in FIG. 1 during real life FGIs. Ionizing radiation dose measurements were made with optically stimulated, luminescent nanoDot detectors (Landauer, Glenwood, IL) with readout using a Landauer microSTARii medical dosimetry system (Landauer, Inc., Glenwood, IL). The nanoDot detectors were annealed with fluorescent light and a background count obtained prior to each use in order to minimize measurement errors.

Phantom Study

Ocular radiation doses with three forms of leaded eyewear were assessed in a controlled phantom study. The eyewear utilized in this study included standard leaded eyewear, leaded eyewear with built-in leaded side-shields, and a modified eyewear device (i.e., an eyewear comprising a custom designed removable safety eyewear shielding device). The standard eyewear was Phillips Model 808 Wraparound Radiation Safety Glasses (Phillips Safety Products Inc., Middlesex, NJ), and the eyewear with built-in leaded side-shields were Burlington Medical ES77S Radiation Glasses with Side-Shield (Burlington Medical LLC, Newport News, VA). The customized device comprised radiation glasses with an additional 0.75 mm of lead shielding attached to the lateral and inferior borders of the glasses frame, molded to the operator's face to protect against oblique radiation exposure (FIG. 1).

Figure 2:
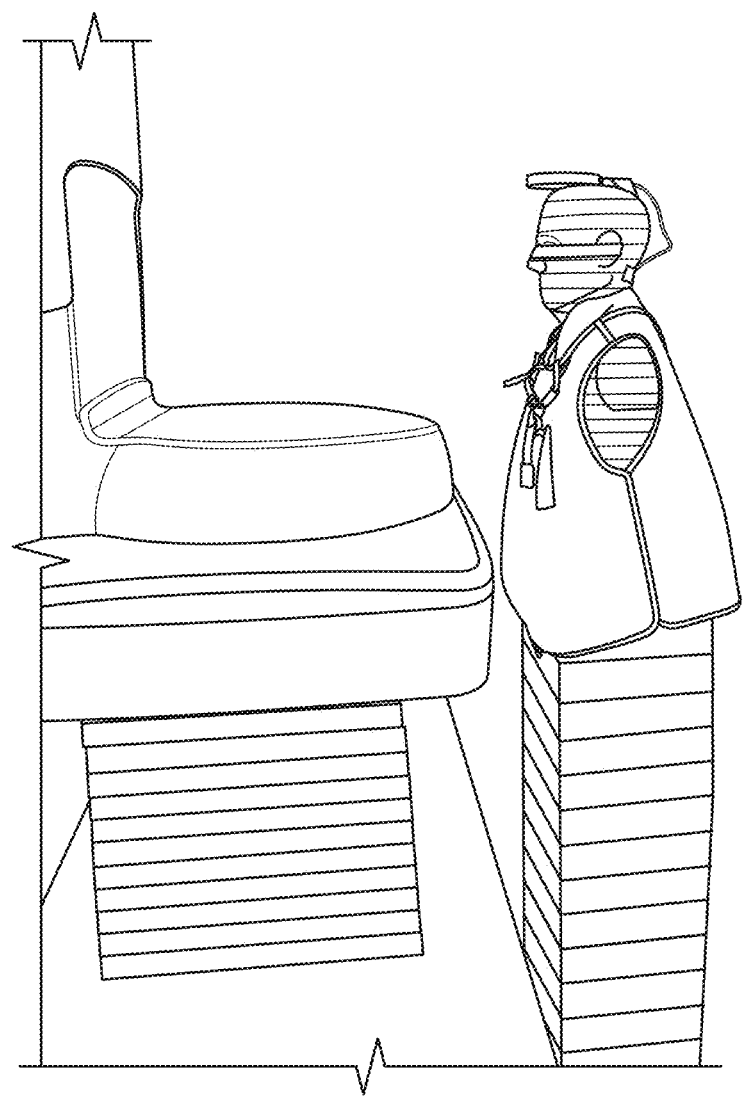
FIG. 2 illustrates an anthropomorphic head phantom positioned in fluoroscopy suite to represent a primary operator performing right femoral access.
Figure 3:
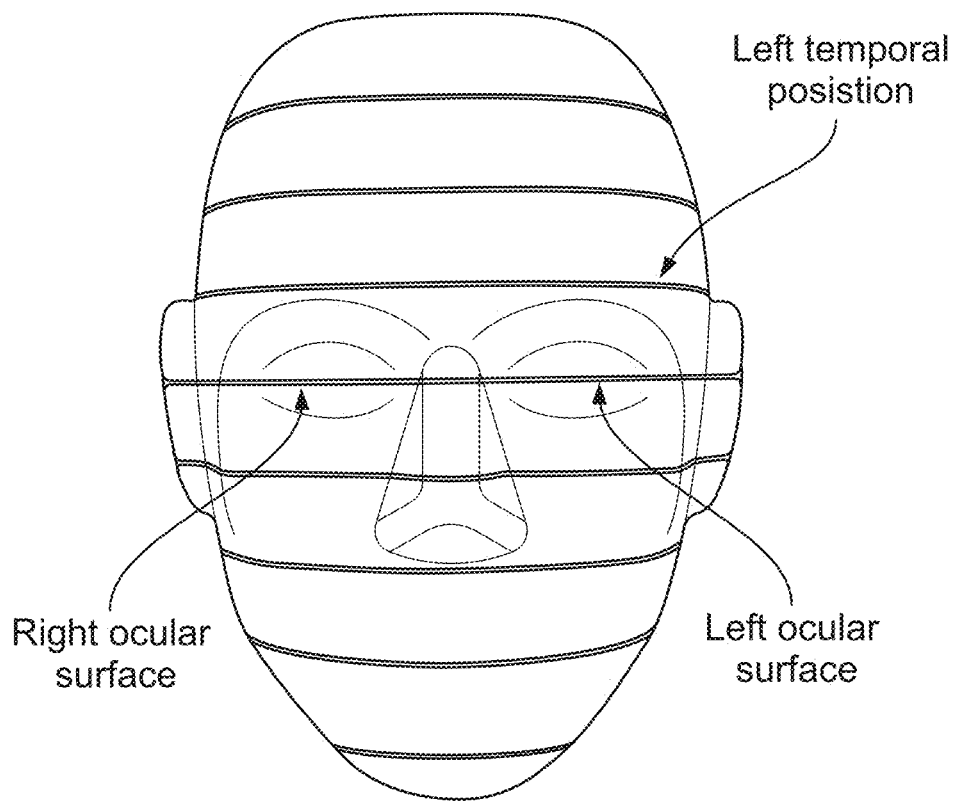
FIG. 3 illustrates a frontal view of anthropomorphic head phantom with nanoDot positions labeled: right ocular surface and left ocular surface, left temporal position.
Figure 4:
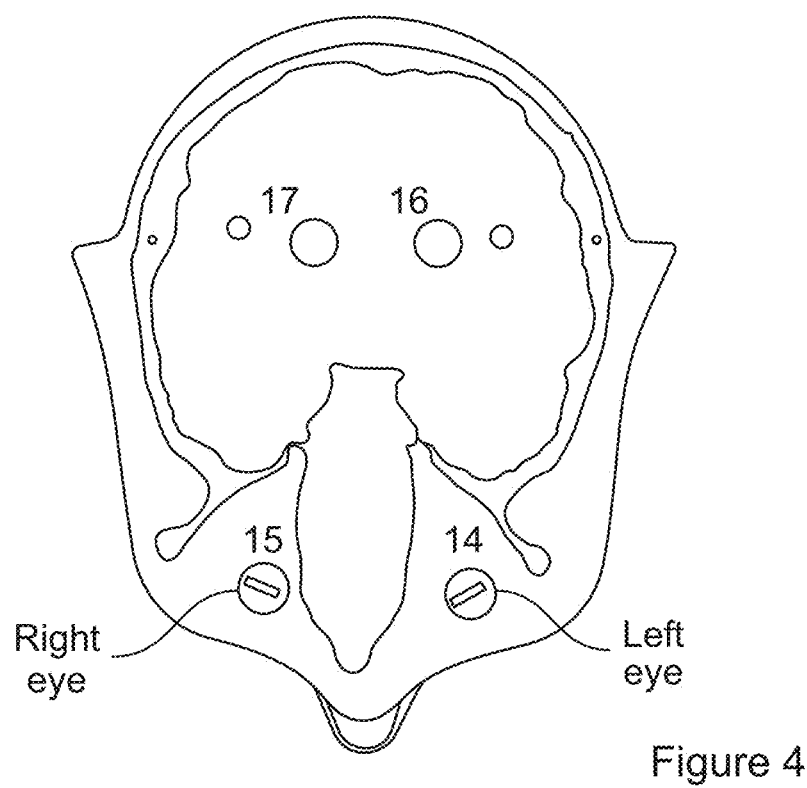
FIG. 4 illustrates the internal ocular spaces of head phantom. The right and left eye nanoDot locations are labeled, and these positions were used to measure lens radiation dose.

The simulated experiments were performed using an anthropomorphic head phantom (ATOM model-701:CIRS, Norfolk, VA). The phantom was positioned to represent that of a primary operator performing right femoral access (FIG. 2). Fluorography was performed on a stacked acrylic sheets (25 cm) to simulate patient scatter from an 80 kVp beam with an exposure time sufficient to achieve a 5 Gy reference-air-kerma reading separately for each eyewear type and a no-eyewear control. NanoDot detectors were placed inside the bilateral ocular spaces of the phantom (at the lens position), and at the surface of both eyes (cornea position) within the protection of the leaded eyewear. Additional nanoDots were also placed immediately below and outside the protective eyewear at both corneal positions (FIGS. 3 and 4). Each experiment (three forms of eyewear and no-eyewear) was repeated four times.

Radiation dose levels for all readings were compared to control values and reported as relative dose reductions. The control values were defined as the radiation doses at each location without any eyewear protection. Mean and standard deviation of relative dose was calculated for each eyewear at each location. Doses received with different eyewear was compared using a linear mixed model with repeated measurements. Heteroscedasticity was addressed by adjusting denominator degrees of freedom. A Dunnett adjustment was performed for all comparisons to the nanoDot control locations. Mean and standard error of the differences were estimated. To show the radiation doses at each nanoDot location the relative doses for each control location was estimated as a percentage of the left corneal eye control dose.

Without eyewear protection, the right eye dose was 48% of the left eye dose (p<0.001). The right eye doses were also not significantly reduced by any ocular design. Left-side control doses (left lens, cornea and temporal location without any eyewear) were not significantly different from each other. Without any eyewear, the doses at these locations were considered to be 100%. Relative mean dose and standard deviation values for every nanoDot location of each eyewear type compared to the controls are shown in Table 1. Standard eyewear showed no significant dose reduction for any measurement position compared to the no-eyewear control. The eyewear with side-shield had no significant dose decrease at the cornea or lens position, but did significantly lower dose at the left temporal position (p<0.001). Modified eyewear had significantly lower dose at all positions (all p values <0.001).

Clinical Study

Physician eye radiation dose measurements were collected during 60 FGIs. For all cases the operator was at the patient's right femoral access position and the fluoroscope was on the left side of the patient. The attenuating efficacy of two types of eyewear (standard lead eyewear and modified eyewear. i.e., an eyewear comprising a custom designed removable safety eyewear shielding device) were tested by attaching nanoDots to the primary operator's face directly underneath the left eye, inside the eyewear coverage and directly below and outside of the eyewear coverage. 30 FGIs were performed with the operator wearing standard lead eyewear and 30 FGIs were performed wearing the modified design. Institutional Board Review (IRB) approval and consent of the patient were waived for this study, as it was deemed quality improvement, not meeting the definition of human subject research and intended only for the improvement of local processes.

The relative dose reduction to the left eye provided by the protective eyewear was defined as the dose from the nanoDot within the protection of the eyewear divided by the dose from the nanoDot immediately under and outside the protective eyewear. Means and standard deviations were calculated. An analysis of covariance (ANCOVA) model was used to test the difference in percent reduction between the modified eyewear and standard leaded eyewear.

P-value of less than 0.05 was considered as statistically significant. SAS 9.4 (SAS Institute, Inc., Cary NC) was used for analysis.

Figure 5:
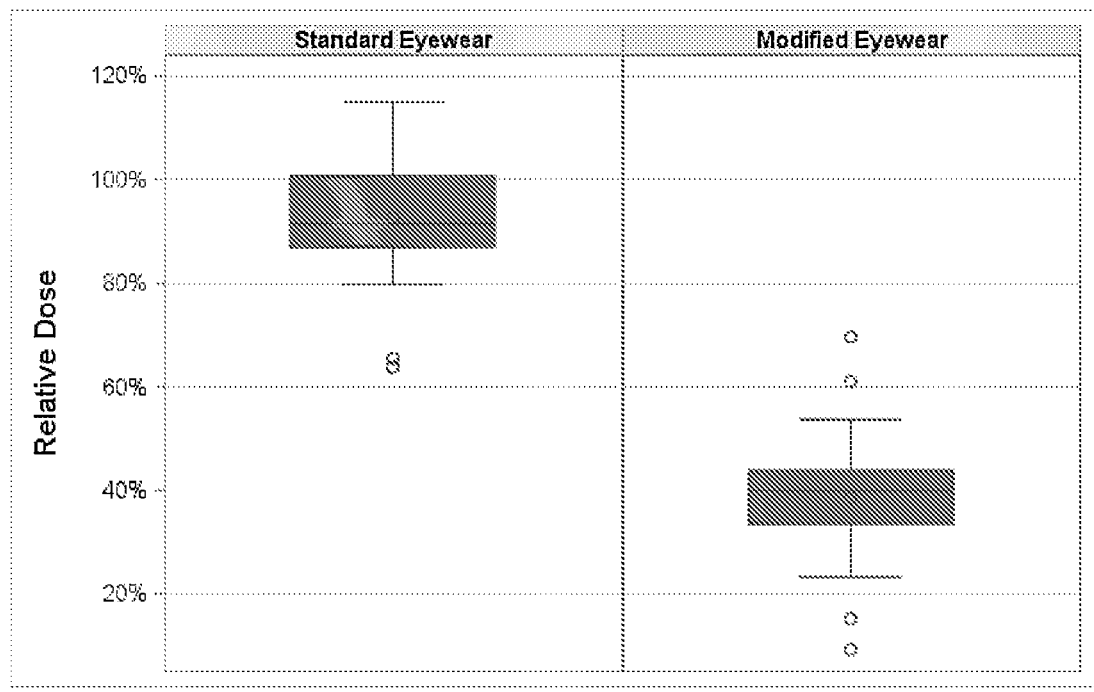
FIG. 5 illustrates left eye relative dose reduction wearing standard and modified eyewear during FGIs.

Mean and standard deviation values of the relative dose reductions for standard and modified eyewear are shown in FIG. 5. No significant dose reduction to the left eye was noted when using standard eyewear during FGIs. On average, the modified eyewear reduced left eye radiation dose to 39%±12% (p<0.0001).

TABLE 1

Dose reduction for each eyewear type and nanoDot location compared to the no eyewear control for the phantom study.

| Eyewear | Left Cornea | Left Lens | Left Temporal | Right Cornea | Right Lens |
| --- | --- | --- | --- | --- | --- |
| Standard Eyewear | 88% ± 3% | 99% ± 4% | 96% ± 5% | 95% ± 10% | 100% ± 14% |
| Eyewear With Side-Shield | 97% ± 13% | 96% ± 5% | 65% ± 8%* | 102% ± 9% | 100% ± 6% |
| Modified Eyewear | 14% ± 1%* | 20% ± 3%* | 9% ± 1%* | 91% ± 10% | 84% ± 10% |

*denotes p < 0.001

Brain dose data is shown in Table 2.

TABLE 2

| Setup | Left Brain | Left Cornea | Left Lens | Left Temporal | Right Cornea | Right Lens |
| --- | --- | --- | --- | --- | --- | --- |
| No Eyewear | 259.30 ± 34.41 | 781.00 ± 142.73 | 518.65 ± 76.44 | 783.90 ± 112.14 | 401.45 ± 74.89 | 176.15 ± 24.02 |
| Standard Eyewear | 258.93 ± 12.74 | 740.93 ± 51.30 | 542.07 ± 30.31 | 791.40 ± 33.34 | 417.67 ± 48.09 | 186.33 ± 25.58 |
| Eyewear With Side-Shield | 247.60 ± 13.91 | 812.33 ± 57.19 | 525.47 ± 21.55 | 533.47 ± 55.55 | 446.27 ± 38.06 | 187.27 ± 21.59 |
| Modified Eyewear | 154.50 ± 9.46 | 106.45 ± 21.65 | 104.15 ± 7.09 | 67.35 ± 7.19 | 367.85 ± 86.41 | 147.15 ± 22.67 |

P values
Modified vs standard: 0.0004
Side-shield vs standard: 0.4734

This prospective, single-center study included 60 FGIs; 30 with traditional eyewear and 30 with the modified design described herein. There was no significant eye radiation dose reduction (p>0.05) with the standard eyewear or leaded side-shield eyewear in both the simulated and clinical settings. In the simulated environment, the modified design resulted in an 86% radiation dose reduction to the surface of the left eye, and an 80% reduction in left lens radiation dose (p<0.0001). In the clinical FGIs, the modified eyewear led to a 62% left ocular radiation dose reduction (p<0.0001).

DISCUSSION

The current guidelines regarding occupational radiation exposure set forth by the International Commission on Radiological Protection (ICRP) state that interventionalists should reduce their ocular lens exposure to 20 mSv a year averaged over 5 years, with no single year exceeding 50 mSv.[7] Despite the ICRP recommendations, several epidemiological studies have found that 38-60% of interventionalists exceed this radiation dose limit.[8,9] The use of lead-equivalent eyewear as safety equipment is encouraged; however, our results indicate that the radiation protection provided by commercially-available eyewear is minimal to none. Other authors have corroborated these findings[4, 10, 11]. Each of the aforementioned studies found no difference in the right eye dose with any eyewear type. We concur with this finding. In the geometric orientation of the FGIs and phantom experiments, as described above, the right eye is further from the radiation source. The majority of radiation to the right eye in this scenario is from scatter radiation after attenuation through the facial bones.[10-12] Therefore, the right eye dose is significantly lower than the left eye dose and is not affected by external ocular coverage.

The addition of leaded side shields do not lower eye dose. There is no significant dose decline in left eye dose in the clinical experiments or in the left corneal or lens doses in the phantom experiments for standard leaded eyewear having leaded side shields (see Table 1). This is because the largest source of radiation scatter in an operation is the patient, meaning that the majority of radiation will be incident upon the interventionalist from inferior and oblique angles. As the leaded side-shields are designed to protect from only direct lateral radiation exposure, the wearer's eyes remain susceptible to the same radiation burden as if no side-shields were worn.

In contrast the devices described herein significantly decrease left eye dose. By molding shielding to the inferior and lateral borders of the eyewear, the air gap is eliminated and the left eye dose is reduced. In head-phantom experiments, the custom designed removable safety eyewear shielding device reduced the radiation dose to the left eye surface and left ocular lens by over 80% (p<0.0001). In the clinical arm, the left eye dose was reduced by 61% (p<0.0001) using the custom design removable device. The variation in dose reduction in the phantom experiment compared to the clinic experiment can be accounted for by the movements of the operator's head and body position relative to the radiation source during live FGIs. Real life conditions cannot be mimicked by the static phantom measurements. As operators move around the room, change head position, and alter gantry angulation, the scatter angles to the eyes will change. Nonetheless, even with all the variability of a live FGI an overall dose decline to the left eye of 61% is profound and has significant clinical relevance. The phantom and clinical studies were performed using custom designed removable safety eyewear shielding devices, and provided protection against oblique radiation as described in Example 1. The disposable removable safety eyewear shielding device described herein, also comprises shielding panels made of radioprotective material. The disposable removable safety eyewear shielding device is expected to work similarly to the custom design removable safety eyewear, and to provide similar protection against oblique radiation, by removing gaps between a safety eyewear and a user's face.

It is noted that in the clinical experiment "eye dose" was extrapolated from nanoDots extremely close to, but not obviously attached to the eye of the operator. The left eye dose was therefore not actual lens dose as it was in the phantom experiment. In the phantom study each experiment was repeated 4 times for consistency; however, each repeated experiment was not performed on the same day. Therefore small fluctuations in fluoroscopic setup and phantom position could result in minimal variability to the eye dose. Finally, for both experiments, nanoDots were randomly chosen for each location and small differences in dose sensitivity will contribute to minor measurement variability.

CONCLUSION

There is a significant body of literature establishing a link between ionizing radiation exposure and cataract formation in interventionalists,[13] with several reports showing cataract development occurring at cumulative doses as low as 100 mGy.[14-16] Given that lens opacification can have a profound impact on a surgeon's ability to operate, it is of paramount importance that effective radiation safety eyewear be available to all practicing interventionalists. Currently available leaded eyewear is ineffective at reducing left ocular dose. Modifying leaded glasses with additional shielding devices importantly eliminates the air gap and significantly reduces left eye dose. A shielding device can be a custom designed removable safety eyewear shielding device comprising a left shielding panel, comprising an inferior panel and a lateral panel; a right shielding panel, comprising an inferior panel and a lateral panel; and a nasal bridge shielding panel, molded to fit a user's face. Alternatively, a shielding device can be a disposable removable safety or personal eyewear shielding device comprising a U-shaped shielding panel comprising an inferior portion, a lateral portion, and a nasal bridge portion. Both of these modifications will allow for meaningful radiation attenuation and will aid in the prevention of health complications following long-term occupational radiation exposure for busy interventionalists.

Example 2: Detachable Shielding Panel Significantly Decreases Operator Ipsilateral Eye and Brain Dose During Fluoroscopically Guided Interventions

Objective

Standard leaded eyewear and leaded surgical caps do not decrease ocular or brain radiation dose, and do not protect operators from the risk of cataracts and brain tumors. A lead equivalent face shield which can be attached to any eyewear, that is conformable around the operator's face, and attaches to the surgical mask has been designed. The aim was to evaluate the efficacy of this novel shield in lowering both operator ipsilateral ocular and brain radiation dose when attached to either leaded or non-leaded eyewear.

Methods

The attenuating efficacy of leaded eyewear alone and leaded and non-leaded eyewear with removable eyewear shielding device as described herein attached were tested and compared to a control of no eyewear or face shield protection. Simulated experiments were performed using an anthropomorphic head phantom (ATOM model-701:CIRS, Norfolk, VA) to measure ocular lens, midbrain and temporal lobe radiation. Optically stimulated, luminescent nanoDot detectors (Landauer,Glenwood, Ill) were placed inside the ocular, temporal lobe, and midbrain spaces of the phantom, and at the surface of the left eye within and outside the eyewear. The phantom was positioned to represent a primary operator performing right femoral access. Fluorography was performed on a plastic scatter phantom at 80 kVp for an exposure of 3 Gy reference-air-kerma for each eyewear type. Each experiment was repeated 4 times for accuracy. Means and standard errors were calculated using a pooled linear mixed model with repeated measurements.

Results

There was no statistically significant ocular or brain dose reduction when wearing leaded eyewear compared to no eyewear protection. With an eyewear shielding device described herein attached to leaded glasses, the dose reductions for the lens, temporal lobe and midbrain were 88% (P<0001), 80% (P<0.0001), and 83% (P<0.001) respectively. When the modification was attached to nonleaded glasses, the dose reductions for the lens, temporal lobe and midbrain were 84% (P<0.001), 70% (P<0.001) and 80% (p<0.001). There was no statistical difference between lens and brain radiation doses when the modification was attached to leaded or nonleaded glasses.

CONCLUSIONS

Leaded eyewear alone does not decrease ocular radiation dose. Attaching a lightweight, lead equivalent shield to either leaded and nonleaded glasses, provides lateral and inferior protection from oblique X-rays and significantly decreases operator ipsilateral ocular and brain dose during FGiS. The radiation protection was similar when the attachment was added to leaded and nonleaded glasses supporting that any choice of eyewear can offer radiation protection when this attachment is utilized.

REFERENCES

1. Vano E, Kleiman N J, Duran A, Romano-Miller M, Rehani M M. Radiation-associated lens opacities in catheterization personnel: results of a survey and direct assessments. J Vasc Interv Radiol. 2013;24:197-204

2. Stahl C M, Meisinger Q C, Andre M P, Kinney T B, Newton I G. Radiation Risk to the Fluoroscopy Operator and Staff. AJR Am J Roentgenol. 2016;207:737-744

3. Ko S, Kang S, Ha M, et al. Health Effects from Occupational Radiation Exposure among Fluoroscopy-Guided Interventional Medical Workers: A Systematic Review. J Vasc Interv Radiol. 2018;29:353-366

4. Fetterly K, Schueler B, Grams M, et al. Head and Neck Radiation Dose and Radiation Safety for Interventional Physicians. JACC Cardiovasc Interv. 2017;10:520-528

5. Domienik J, Bissinger A, Grabowicz W, et al. The impact of various protective tools on the dose reduction in the eye lens in an interventional cardiology-clinical study. J Radiol Prot. 2016;36:309-318

6. Carinou E, Ferrari P, Bjelac O C, et al. Eye lens monitoring for interventional radiology personnel: dosemeters, calibration and practical aspects of H p (3) monitoring. A 2015 review. J Radiol Prot. 2015;35:R17-34

7. Dauer L T, Ainsbury E A, Dynlacht J, et al. Guidance on radiation dose limits for the lens of the eye: overview of the recommendations in NCRP Commentary No. 26. Int J Radiat Biol. 2017;93:1015-1023

8. Vanhavere F, Carinou E, Domienik J, et al. Measurements of eye lens doses in interventional radiology and cardiology: Final results of the ORAMED project. Radiat Meas. 2011;46:1243-1247

9. Jacob S, Donadille L, Maccia C, et al. Eye lens radiation exposure to interventional cardiologists: a retrospective assessment of cumulative doses. Radiat Prot Dosimetry. 2013;153:282-293

10. van Rooijen B D, de Haan M W, Das M, et al. Efficacy of radiation safety glasses in interventional radiology. Cardiovasc Intervent Radiol. 2014;37:1149-1155

11. Sturchio G M, Newcomb R D, Molella R, et al. Protective eyewear selection for interventional fluoroscopy. Health Phys. 2013;104:S11-16

12. Geber T, Gunnarsson M, Mattsson S. Eye lens dosimetry for interventional procedures—Relation between the absorbed dose to the lens and dose at measurement positions. Radiat Meas. 2011;46:1248-1251

13. Seals K F, Lee E W, Cagnon C H, Al-Hakim R A, Kee S T. Radiation-Induced Cataractogenesis: A Critical Literature Review for the Interventional Radiologist. Cardiovasc Intervent Radiol. 2016;39:151-160

14. Ainsbury E A, Barnard S, Bright S, et al. Ionizing radiation induced cataracts: Recent biological and mechanistic developments and perspectives for future research. Mutat Res. 2016;770:238-261

15. Seals K, Trieu H, Kee S, Lee E W. Cataract Development in Vascular Intervention. Endovascular Today. 2016; 15:73-76

16. Shore R E. Radiation and cataract risk: Impact of recent epidemiologic studies on ICRP judgments. Mutat Res. 2016;770:231-23718.

17. Ko S, Kang S, Ha M, et al. Health Effects from Occupational Radiation Exposure among Fluoroscopy-Guided Interventional Medical Workers: A Systematic Review. J Vasc Interv Radiol. 2018;29:353-36620.

What is claimed is:

1. A removable eyewear shielding device comprising:
a shielding panel comprising:
   i) an inferior curved edge (20),
   ii) a superior curved edge (30),
   iii) a thin edge (40) joining a first end of the inferior curved edge (20a) to a first end of the superior curved edge (30a), and
   iv) a wide edge (50) joining a second end of the inferior curved edge (20b) to a second end of the superior curved edge (30b);
wherein the removable eyewear shielding device is configured to be attached to and detached from an eyewear frame comprising a superior lens frame portion (1), an inferior lens frame portion (2), a first lateral lens frame portion (3) joining the inferior lens frame portion (2) to the superior lens frame portion (1) at a hinge (7) side of the eyewear frame, a second lateral lens frame portion (4) joining the inferior lens frame portion (2) to the superior lens frame portion (1), a nasal bridge (5), and a temple (8), and
wherein an inferior portion of the shielding panel (12) is configured to extend from the inferior lens frame portion (2) of the eyewear frame to a position below a user's lower cheekbone when the removable eyewear shielding is attached to the nasal bridge (5) and the temple (8) of the eyewear frame.

2. The removable eyewear shielding device of claim 1, wherein the shielding panel comprises a lateral portion (11) and a nasal bridge portion (13).

3. The removable eyewear shielding device of claim 1, wherein the inferior curved edge (20) comprises one or more adhesive strips, one or more inferior conformable wires (21), or a combination thereof.

4. The removable eyewear shielding device of claim 3, wherein the one or more adhesive strips or one or more inferior conformable wires (21) are configured to extend from the user's nose to the user's upper lateral cheekbone.

5. The removable eyewear shielding device of claim 1, wherein the wide edge (50) comprises a slide-on pocket (51).

6. The removable eyewear shielding device of claim 5, wherein the slide-on pocket is configured to directly fasten the shielding device to the temple (8) of the eyewear frame.

7. The removable eyewear shielding device of claim 1, wherein the shielding panel comprises a radio-protective material located on an interior side of the shielding panel, or inserted inside a pocket within the shielding panel.

8. The removable eyewear shielding device of claim 1, wherein the superior curved edge (30) comprises one or more superior conformable wires (31).

9. The removable eyewear shielding device of claim 8, wherein the one or more superior conformable wires (31) extend from the hinge (7) of the eyewear frame to the thin edge (40).

10. The removable eyewear shielding device of claim 1, wherein the superior curved edge (30) comprises one or more adhesive strips.

11. The removable eyewear shielding device of claim 1, wherein one or more inferior conformable wires (21), one or more superior conformable wires (31), or both are configured to be moldable around and across the user's nose bridge.

12. The removable eyewear shielding device of claim 1, wherein the shielding panel is a U-shaped shielding panel.

13. The removable eyewear shielding device of claim 12, wherein one or more superior conformable wires (31) are configured to be moldable along the first lateral lens frame portion (3), the inferior lens frame portion (2), and the second lateral lens frame portion (4) of the eyewear frame.

14. The removable eyewear shielding device of claim 12, wherein the thin edge (40) comprises an adhesive piece (41) to fasten the shielding device around the nasal bridge of the eyewear frame.

15. A eyewear comprising:
a) the removable eyewear shielding device of claim 1,
b) the eyewear frame, and
c) a shielding lens,
wherein the removable eyewear shielding device is attached to the eyewear frame.

16. The eyewear of claim 15, wherein the removable eyewear shielding device is attached to the right side of the eyewear frame, to the left side of the eyewear frame, or to the right side and the left side of the eyewear frame.

17. A method of reducing eye radiation exposure, reducing ipsilateral brain radiation exposure, reducing FGI-induced lens opacification, reducing cataract development, protecting an eye or ipsilateral brain from radiation exposure, or a combination thereof in the user comprising providing to the user the removable eyewear shielding device of claim 1, for use during exposure to ionizing radiation, thereby reducing the amount of ionizing radiation reaching the user's eye or ipsilateral brain.

18. The method of claim 17, wherein the shielding device extends from a first lateral frame of the eyewear frame to the user's nose, from an inferior frame of the eyewear frame to the user's lower cheekbone or jaw, and from a second lateral frame and from a temple of the eyewear frame to the user's upper lateral cheekbone.

19. The method of claim 17, wherein one or more adhesive strips, one or more inferior conformable wires, or both are in contact with the user's nose, lower cheekbone or jaw and upper lateral cheekbone to eliminate any space gap between the removable shielding device and the operator's face.

20. The method of claim 17, wherein the removable eyewear shielding device protects the eyes and the ipsilateral brain of the user from oblique radiation exposure.

21. The method of claim 17, wherein a space between a superior frame of the eyewear frame and the user's face is open to reduce fogging and to increase the user's comfort.

22. A removable eyewear shielding device comprising:
a shielding panel comprising:
i) an inferior curved edge (20),
ii) a superior curved edge (30),
iii) a thin edge (40) joining a first end of the inferior curved edge (20a) to a first end of the superior curved edge (30a),
iv) a wide edge (50) joining a second end of the inferior curved edge (20b) to a second end of the superior curved edge (30b),
v) a lateral portion (11), and
vi) a nasal bridge portion (13);
wherein the removable eyewear shielding device is configured to be attached to and detached from an eyewear frame comprising a superior lens frame portion (1), an inferior lens frame portion (2), a first lateral lens frame portion (3) joining the inferior lens frame portion (2) to the superior lens frame portion (1) at a hinge (7) side of the eyewear frame, and a second lateral lens frame portion (4) joining the inferior lens frame portion (2) to the superior lens frame portion (1),
wherein an inferior portion of the shielding panel (12) is configured to extend from the inferior lens frame portion (2) of the eyewear frame to a user's lower cheekbone, and
wherein the lateral portion of the shielding panel (11) is configured to extend from the first lateral lens frame portion (3) and from a temple (8) of the eyewear frame to the user's upper lateral cheekbone.

23. A removable eyewear shielding device comprising:
a shielding panel comprising:
i) an inferior curved edge (20),
ii) a superior curved edge (30),
iii) a thin edge (40) joining a first end of the inferior curved edge (20a) to a first end of the superior curved edge (30a),
iv) a wide edge (50) joining a second end of the inferior curved edge (20b) to a second end of the superior curved edge (30b),
v) a lateral portion (11), and
vi) a nasal bridge portion (13);
wherein the removable eyewear shielding device is configured to be attached to and detached from an eyewear frame comprising a superior lens frame portion (1), an inferior lens frame portion (2), a first lateral lens frame portion (3) joining the inferior lens frame portion (2) to the superior lens frame portion (1) at a hinge (7) side of the eyewear frame, and a second lateral lens frame portion (4) joining the inferior lens frame portion (2) to the superior lens frame portion (1), wherein an inferior portion of the shielding panel (12) is configured to extend from the inferior lens frame portion (2) of the eyewear frame to a user's lower cheekbone, and wherein the nasal bridge portion (13) of the shielding panel is configured to extend from the second lateral lens frame (4) of the eyewear frame to the user's nose.

* * * * *